US009439979B2

(12) United States Patent
Chiorini et al.

(10) Patent No.: US 9,439,979 B2
(45) Date of Patent: Sep. 13, 2016

(54) EPIDERMAL GROWTH FACTOR RECEPTOR (EGFR) AND METHODS OF USE IN ADENOVIRAL-ASSOCIATED VIRUS TYPE 6 (AAV6) TRANSDUCTION

(71) Applicant: The United States of America, as represented by the Secretary, Department of Health and Human Services, Washington, DC (US)

(72) Inventors: John Chiorini, Dayton, MD (US); Melodie L. Weller, Silver Spring, MD (US); Michael Schmidt, Kensington, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 3 days.

(21) Appl. No.: 14/301,973

(22) Filed: Jun. 11, 2014

(65) Prior Publication Data
US 2014/0296326 A1 Oct. 2, 2014

Related U.S. Application Data

(62) Division of application No. 12/879,142, filed on Sep. 10, 2010, now Pat. No. 8,808,684.

(51) Int. Cl.
| | |
|---|---|
| A61K 31/70 | (2006.01) |
| C12N 15/00 | (2006.01) |
| C07H 21/04 | (2006.01) |
| A61K 48/00 | (2006.01) |
| C07K 14/71 | (2006.01) |
| C12N 15/86 | (2006.01) |
| A61K 31/522 | (2006.01) |
| A61K 45/06 | (2006.01) |

(52) U.S. Cl.
CPC .......... *A61K 48/005* (2013.01); *A61K 31/522* (2013.01); *A61K 45/06* (2013.01); *A61K 48/0008* (2013.01); *C07K 14/71* (2013.01); *C12N 15/86* (2013.01); *C07H 21/04* (2013.01); *C12N 2750/14143* (2013.01); *C12N 2750/14145* (2013.01)

(58) Field of Classification Search
CPC .......... A61K 31/522; A61K 48/0008; A61K 48/005; C12N 15/86; C12N 2750/14143; C12N 2750/14145; C07H 21/04
USPC ....... 514/1, 44 R; 435/320.1; 536/23.5, 23.7, 536/23.72
See application file for complete search history.

(56) References Cited

U.S. PATENT DOCUMENTS

| | | | |
|---|---|---|---|
| 6,156,303 | A | 12/2000 | Russell et al. |
| 2003/0223971 | A1 | 12/2003 | Kurtzman et al. |
| 2005/0095227 | A1 | 5/2005 | Rosenzweig et al. |
| 2009/0239236 | A1 | 9/2009 | Mass |
| 2010/0129405 | A1 | 5/2010 | Schmidt et al. |
| 2011/0275529 | A1 | 11/2011 | Heilbronn |

FOREIGN PATENT DOCUMENTS

| | | |
|---|---|---|
| WO | WO 99/64569 A1 | 12/1999 |
| WO | WO 00/39311 A1 | 7/2000 |

OTHER PUBLICATIONS

Zaiss et al., 2005, Current Gene therapy, vol. 5, p. 323-331.*
Selot et al., 2013, Current Pharmaceutical Biotechnology, vol. 14, No. 12, p. 1-11.*
Rogers et al., 2011, Frontiers in Microbiology, vol. 2, Article 194, p. 1-10.*
Lenzi et al., 2014, NCBI Bookshelf, A Service of the National Library of Medicine, National Institute of Health, Oversight and Review of Clinical Gene Transfer Protocols: Assessing the Role of the Recombinant DNA Advisory Committee. Washington (DC): National Academies Press (US), pp. 1-16.*
Alisky et al., "Transduction of murine cerebellar neurons with recombinant FIV and AAV5 vectors," *Molecular Neuroscience*, 11 (12), 2669-2673 (2000).
Blankinship et al., "Efficient Transduction of Skeletal Muscle Using Vectors Based on Adeno-associated Virus Serotype 6," *Molecular Therapy*, 10 (4), 671-678 (2004).
Castro et al., "Gene therapy for Parkinson's disease: recent achievements and remaining challenges," *Histol Histopathol.*, 16, 1225-1238 (2001).
Chiorini et al., "Epidermal Growth Factor Receptor is a Receptor for Adeno-Associated Virus Serotype 6," *Molecular Therapy*, 17, Supp 1, S146 (2009).
dos Santos Coura, "The state of the art of adeno-associated virus-based vectors in gene therapy" *Virology Journal*, 4 (99), 1-7 (2007).
Fukui et al., "Suicide gene therapy for human oral squamous cell carcinoma cell lines with adeno-associated virus vector," *Oral Oncology*, 37, 211-215 (2001).
Gorecki et al., "Prospects and problems of gene therapy: an update," *Experi. Opin. Emerging Drugs*, 6(2), 187-198 (2001).
Kanazawa et al, "Suicide gene therapy using AAV-HSVtk/ganciclovir in combination with irradiation results in regression of human head and neck cancer xenografts in nude mice," *Gene Therapy*, 10, 51-58 (2003).

(Continued)

Primary Examiner — Shin Lin Chen
(74) Attorney, Agent, or Firm — Leydig, Voit & Mayer (57) ABSTRACT

Comparative gene analysis (CGA) was combined with pathway visualization software to identify a positive correlation between AAV6 transduction and epidermal growth factor receptor (EGFR) expression. It was found that EGFR is necessary for vector internalization and functions as a co-receptor for AAV6. The identification and characterization of AAV6's requirement of EGFR expression for high transduction activity has allowed construction of recombinant AAV6 vectors which are capable of targeting and killing specific types of head and neck tumors that because of this high EGFR activity, were until now, refractory to current therapies.

18 Claims, 9 Drawing Sheets

(56) References Cited

OTHER PUBLICATIONS

Lango et al., "Targeting growth factor receptors: integration of novel therapeutics in the management of head and neck cancer," *Current Opinion in Oncology*, 13(3), 168-175 (2001).
Li et al., "Adeno-associated virus vectors: potential applications for cancer gene therapy," *Cancer Gene Ther.*, 12 (12), 913-925 (2005).
Lowenstein et al., "Progress and challenges in viral vector-mediated gene transfer to the brain," *Current Opinion in Molecular Therapeutics*, 4(4), 359-371 (2002).
Schmidt et al., "Adeno-Associated Virus Type 12 (AAV12): a Novel AAV Serotype with Sialic Acid- and Heparan Sulfate Proteoglycan-Independent Transduction Activity," *J. Virology*, 82 (3), 1399-1406 (2008).
Song et al., "Functional Cystic Fibrosis Transmembrane Conductance Regulator Expression in Cystic Fibrosis Airway Epithelial Cells by AAV6.2-Mediated Segmental Trans-Splicing," *Hum. Gene Ther.*, 20, 267-281 (2009).
Ussher et al., "Optimized Transduction of Human Monocyte-Derived Dendritic Cells by Recombinant Adeno-Associated Virus Serotype 6 (rAAV6)," *Human Gene Therapy*, 1-38 (2010).
Weller et al., "Epidermal growth factor receptor is a co-receptor for adeno-associated virus serotype 6," *Nature Medicine*, 16 (6), 662-664 (2010).
Xie et al., "Combination of EGFR, HER-2/neu, and HER-3 Is a Stronger Predictor for the Outcome of Oral Squamous cell Carcinoma Than Any Individual Family Members," *Clinical Cancer Research*, 5, 4164-4174 (1999).
Zaiss et al., "Immune Response to Adeno-Associated Virus Vectors," *Current Gene Therapy*, 5, 323-331 (2005).
Zincarelli et al., "Analysis of AAV Serotypes 1-9 Mediated Gene Expression and Tropism in Mice After Systemic Injection," *Molecular Therapy*, 16 (6), 1073-1080 (2008).

\* cited by examiner

EPIDERMAL GROWTH FACTOR RECEPTOR (EGFR) AND METHODS OF USE IN ADENOVIRAL-ASSOCIATED VIRUS TYPE 6 (AAV6) TRANSDUCTION

CROSS-REFERENCE TO RELATED APPLICATIONS

This patent application is a divisional of copending U.S. patent application Ser. No. 12/879,142, filed Sep. 10, 2010, which is incorporated by reference herein in its entirety.

BACKGROUND OF THE INVENTION

AAV vectors offer unique advantages over other vector systems in gene therapy applications. Studies have shown that these replication deficient parvovirus vectors can deliver DNA to specific tissues and confer long-term transgene expression in a variety of systems. Although many studies have looked at the tissue-specific expression elicited by each of the AAV serotypes, a true understanding of how AAV transduces these tissues is still unclear. Of the large AAV family, only a few receptors or co-receptors have been identified for any of the parvoviruses. The ability to better target transduction to specific tissues on the basis of the receptors that each serotype uses for entry, is essential to enable users to pick a serotype given the receptor expression in specific tissue, or to exploit altered receptor expression under disease conditions.

AAV6 has been reported to effectively transduce muscle, lung, brain, and multiple types of tumors, including gliomas and lung adenocarcinomas, and to elicit lower serum-neutralizing antibody concentrations when compared with AAV2. As such, there exists a need for improving the treatment of patients suffering from diseases such as cancer, which could be treated by AAV6 vector based gene therapy.

BRIEF SUMMARY OF THE INVENTION

In accordance with the present invention, it was found that the epidermal growth factor receptor (EGFR) is a co-receptor for AAV6 infection in mammalian cells, and is necessary for efficient vector internalization.

In an embodiment, the invention provides a method for introducing a heterologous nucleic acid into a host cell expressing EGFR comprising providing a pharmaceutical composition comprising a recombinant adeno-associated virus (AAV) vector comprising the AAV subtype 6 (AAV6) viral genome, or a functional portion thereof, and containing a heterologous nucleic acid sequence capable of being expressed by the host cell, under conditions which allow transduction of the host cell; and transducing the host cell with the recombinant AAV6 vector.

In a further embodiment, the host cell is a mammalian cell. In addition, in another embodiment, the host cell is a cancer cell. In yet another embodiment, the cancer cell is derived from a tumor of the head or neck.

In an embodiment of the present invention, the heterologous nucleic acid sequence can be either DNA or RNA, and can encode for a polypeptide.

In a further embodiment of the present invention, the heterologous nucleic acid encodes a gene that increases the host cell's susceptibility to a prodrug or cytotoxic agent. For example, in an embodiment, the heterologous nucleic acid can encode an enzyme that when expressed in the cell in the presence of an agent or prodrug, causes modification of the agent into a cytotoxin, which then kills the host cell.

In another embodiment, the method includes a period of time between the administration of a therapeutically effective amount of a pharmaceutical composition comprising a recombinant AAV6 vector which encodes a gene that increases the host cell's susceptibility to a prodrug or cytotoxic agent, and the administration of a therapeutically effective amount of a pharmaceutical composition comprising the specific prodrug or cytotoxic agent. In an embodiment, the method of the present invention includes administration of one or more additional chemotherapeutic agents either concurrently with, or, after administration of the pharmaceutical composition comprising a recombinant AAV6 vector and the administration of a therapeutically effective amount of a pharmaceutical composition comprising the specific prodrug or cytotoxic agent.

DETAILED DESCRIPTION OF THE INVENTION

In accordance with the present invention, it was found that the epidermal growth factor receptor (EGFR) is a co-receptor for AAV6 infection in mammalian cells, and is necessary for efficient vector internalization.

In an embodiment, the invention provides a method for introducing a heterologous nucleic acid into a host cell expressing EGFR comprising providing a pharmaceutical composition comprising a recombinant adeno-associated virus (AAV) vector comprising the AAV subtype 6 (AAV6) viral genome, or a functional portion thereof, and containing a heterologous nucleic acid sequence capable of being expressed by the host cell, under conditions which allow transduction of the host cell; and transducing the host cell with the recombinant AAV6 vector.

In an embodiment of the present invention, the transduction of the host cell can be either in vivo or in vitro.

In a further embodiment, the host cell is a mammalian cell. In addition, in another embodiment, the host cell is a cancer cell. In yet another embodiment, the cancer cell is derived from a tumor of the head or neck.

In an embodiment of the present invention, the heterologous nucleic acid sequence can be either DNA or RNA, and can encode for a polypeptide.

In another embodiment, the heterologous nucleic acid encodes proteins or polypeptides that replace missing or defective proteins required by the cell or subject into which the vector is transferred, or encodes a gene for a missing or defective protein, or can encode a cytotoxic polypeptide that can be directed, e.g., to cancer cells or other cells whose death would be beneficial to the subject.

In a further embodiment of the present invention, the heterologous nucleic acid encodes a polypeptide or protein that increases the host cell's susceptibility to a prodrug or cytotoxic agent, or encodes for a gene for said polypeptide or protein. For example, in an embodiment, the heterologous nucleic acid can encode a gene for an enzyme that when expressed in the cell in the presence of an agent or prodrug, causes modification of the agent into a cytotoxin, which then kills the host cell. For example, in an embodiment, the heterologous nucleic acid can encode at least one of the following enzymes selected from the group consisting of: E. coli nitroreductase, cytosine deaminase, Varicella Zoster-tk, Cytochrome P450 B1 (CYP2B1), carboxypeptidase G2 (CPG2) and E. coli purine nucleoside phosphorylase (ePNP), and the cells are then exposed to an agent or prodrug selected from the group consisting of: CB1954 (5-[aziridin-1-yl]-2,4-dinitrobenzamide), 5-FC (5-Fluorocytosine), araM (6-methoxy purine arabinoside), CPA (cyclophosphamide), benzoic acid mustard glutamates, and 6-methylpurine 2'-deoxyriboside (MePdR) respectively. In another embodiment, the heterologous nucleic acid encodes Herpes Simplex Virus thymidine kinase enzyme (HSV-tk), and the agent is an antiviral agent in the class of nucleotide analogs, such as acyclovir or ganciclovir.

In yet another embodiment of the present invention, the heterologous nucleic acid can also encode EGFR.

In an embodiment, the method includes a period of time between the administration of a therapeutically effective amount of a pharmaceutical composition comprising a recombinant AAV6 vector which encodes a gene that increases the host cell's susceptibility to a prodrug or cytotoxic agent, and the administration of a therapeutically effective amount of a pharmaceutical composition comprising the specific prodrug or cytotoxic agent. In another embodiment, the method of the present invention includes administration of one or more additional chemotherapeutic agents either concurrently with, or, after administration of the pharmaceutical composition comprising a recombinant AAV6 vector and the administration of a therapeutically effective amount of a pharmaceutical composition comprising the specific prodrug or cytotoxic agent.

By "nucleic acid" as used herein includes "polynucleotide," "oligonucleotide," and "nucleic acid molecule," and generally means a polymer of DNA or RNA, which can be single-stranded or double-stranded, synthesized or obtained (e.g., isolated and/or purified) from natural sources, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide. It is generally preferred that the nucleic acid does not comprise any insertions, deletions, inversions, and/or substitutions. However, it may be suitable in some instances, as discussed herein, for the nucleic acid to comprise one or more insertions, deletions, inversions, and/or substitutions.

In an embodiment, the nucleic acids of the invention are recombinant. As used herein, the term "recombinant" refers to (i) molecules that are constructed outside living cells by joining natural or synthetic nucleic acid segments to nucleic acid molecules that can replicate in a living cell, or (ii) molecules that result from the replication of those described in (i) above. For purposes herein, the replication can be in vitro replication or in vivo replication.

The nucleic acids can be constructed based on chemical synthesis and/or enzymatic ligation reactions using procedures known in the art. See, for example, Sambrook et al.

(eds.), *Molecular Cloning, A Laboratory Manual*, 3rd Edition, Cold Spring Harbor Laboratory Press, New York (2001) and Ausubel et al., *Current Protocols in Molecular Biology*, Greene Publishing Associates and John Wiley & Sons, NY (2007). For example, a nucleic acid can be chemically synthesized using naturally occurring nucleotides or variously modified nucleotides designed to increase the biological stability of the molecules or to increase the physical stability of the duplex formed upon hybridization (e.g., phosphorothioate derivatives and acridine substituted nucleotides). Examples of modified nucleotides that can be used to generate the nucleic acids include, but are not limited to, 5-fluorouracil, 5-bromouracil, 5-chlorouracil, 5-iodouracil, hypoxanthine, xanthine, 4-acetylcytosine, 5-(carboxyhydroxymethyl) uracil, 5-carboxymethylaminomethyl-2-thiouridine, 5-carboxymethylaminomethyluracil, dihydrouracil, beta-D-galactosylqueosine, inosine, $N^6$-isopentenyladenine, 1-methylguanine, 1-methylinosine, 2,2-dimethylguanine, 2-methyladenine, 2-methylguanine, 3-methylcytosine, 5-methylcytosine, $N^6$-substituted adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-$N^6$-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3-(3-amino-3-$N^2$-carboxypropyl) uracil, and 2,6-diaminopurine. Alternatively, one or more of the nucleic acids of the invention can be purchased from companies, such as Macromolecular Resources (Fort Collins, Colo.) and Synthegen (Houston, Tex.).

The nucleic acid can comprise a recombinant adeno-associated virus (AAV) vector comprising the AAV subtype 6 (AAV6) viral genome, and containing a heterologous nucleic acid sequence capable of being expressed by the host cell.

The nucleic acids of the invention can be incorporated into a recombinant expression vector. In this regard, the invention provides recombinant expression vectors comprising any of the nucleic acids of the invention. For purposes herein, the term "recombinant expression vector" means a genetically-modified oligonucleotide or polynucleotide construct that permits the expression of an mRNA, protein, polypeptide, or peptide by a host cell, when the construct comprises a nucleotide sequence encoding the mRNA, protein, polypeptide, or peptide, and the vector is contacted with the cell under conditions sufficient to have the mRNA, protein, polypeptide, or peptide expressed within the cell. The vectors of the invention are not naturally-occurring as a whole. However, parts of the vectors can be naturally-occurring. The inventive recombinant expression vectors can comprise any type of nucleotides, including, but not limited to DNA and RNA, which can be single-stranded or double-stranded, synthesized or obtained in part from natural sources, and which can contain natural, non-natural or altered nucleotides. The recombinant expression vectors can comprise naturally-occurring, non-naturally-occurring internucleotide linkages, or both types of linkages. Preferably, the non-naturally occurring or altered nucleotides or internucleotide linkages do not hinder the transcription or replication of the vector.

The recombinant expression vectors of the invention can be prepared using standard recombinant DNA techniques described in, for example, Sambrook et al., supra, and Ausubel et al., supra. Constructs of expression vectors, which are circular or linear, can be prepared to contain a replication system functional in a prokaryotic or eukaryotic host cell. Replication systems can be derived, e.g., from ColE1, 2µ plasmid, SV40, bovine papilloma virus, and the like.

Desirably, the recombinant expression vector comprises regulatory sequences, such as transcription and translation initiation and termination codons, which are specific to the type of host (e.g., bacterium, fungus, plant, or animal) into which the vector is to be introduced, as appropriate and taking into consideration whether the vector is DNA or RNA based.

The recombinant expression vector can include one or more marker genes, which allow for selection of transformed or transfected hosts. Marker genes include biocide resistance, e.g., resistance to antibiotics, heavy metals, etc., complementation in an auxotrophic host to provide prototrophy, and the like. Suitable marker genes for the inventive expression vectors include, for instance, LacZ, green fluorescent protein (GFP), luciferase, neomycin/G418 resistance genes, hygromycin resistance genes, histidinol resistance genes, tetracycline resistance genes, and ampicillin resistance genes.

The term "heterologous nucleic acid sequence" means one or more nucleic acid sequences encoding polypeptides for one or more proteins or enzymes which are not native to AAV6, and which are capable of being expressed when transduced in a host cell, or sequences encoding genes for said one or more proteins or enzymes. In an embodiment of the present invention, the heterologous nucleic acid sequence encodes a gene for an enzyme that is expressed within the host cell, and wherein the enzyme's activity within the host cell, increases the host cell's susceptibility to a particular prodrug or cytotoxic agent. This type of enzyme is also called a "suicide gene." See, for example, *Suicide Gene Therapy: Methods and Reviews*, Springer, Caroline J. (Cancer Research UK Centre for Cancer Therapeutics at the Institute of Cancer Research, Sutton, Surrey, UK), Humana Press, 2004). Examples of combinations of enzyme and prodrug that are capable of being used in the present invention include, for example, HSV-tk and ganciclovir, *E. coli* nitroreductase and CB1954 (5-[aziridin-1-yl]-2,4-dinitrobenzamide), cytosine deaminase and 5-FC (5-Fluorocytosine), Varicella Zoster-tk and araM (6-methoxy purine arabinoside), Cytochrome P450 B1 (CYP2B1) and CPA (cyclophosphamide), carboxypeptidase G2 (CPG2) and benzoic acid mustard glutamates, *E. coli* purine nucleoside phosphorylase (ePNP) and 6-methylpurine deoxyriboside (MePdR).

The heterologous nucleic acid can be a nucleic acid not normally found in the target cell, or it can be an extra copy or copies of a nucleic acid normally found in the target cell. The terms "exogenous" and "heterologous" are used herein interchangeably.

By "functionally linked" is meant that the promoter can promote expression of the heterologous nucleic acid, as is known in the art, and can include the appropriate orientation of the promoter relative to the exogenous nucleic acid. Furthermore, the heterologous nucleic acid preferably has all appropriate sequences for expression of the nucleic acid. The nucleic acid can include, for example, expression control sequences, such as an enhancer, and necessary information processing sites, such as ribosome binding sites, RNA splice sites, polyadenylation sites, and transcriptional terminator sequences.

The heterologous nucleic acid can encode beneficial proteins or polypeptides (e.g., "beneficial" proteins or polypeptides) that replace missing or defective proteins required by the cell or subject into which the vector is transferred, or can encode a cytotoxic polypeptide that can be directed, e.g., to cancer cells or other cells whose death would be beneficial to the subject. The heterologous nucleic acid can also encode antisense RNAs that can bind to, and thereby inactivate, mRNAs made by the subject that encode harmful proteins. The heterologous nucleic acid can also encode ribozymes that can effect the sequence-specific inhibition of gene expression by the cleavage of mRNAs. In one aspect, antisense polynucleotides can be produced from an heterologous expression cassette in an AAV6 vector construct where the expression cassette contains a sequence that promotes cell-type specific expression (Wirak et al., *EMBO* 10:289 (1991)). For general methods relating to antisense polynucleotides, see *Antisense RNA and DNA*, D. A. Melton, Ed., Cold Spring Harbor Laboratory, Cold Spring Harbor, N.Y. (1988). Other examples of heterologous nucleic acids which can be administered to a cell or subject as part of the recombinant AAV6 vector of the present invention can include, but are not limited to, the following: nucleic acids encoding secretory and nonsecretory proteins, nucleic acids encoding therapeutic agents.

In addition, other therapeutic agents may be encoded by heterologous nucleic acids, such as tumor necrosis factors (TNFs), as TNF-$\alpha$; interferons, such as interferon-$\alpha$, interferon-$\beta$, and interferon-$\gamma$, interleukins, such as IL-1, IL-1$\beta$, and ILs-2 through -14; GM-CSF; adenosine deaminase; cellular growth factors, such as lymphokines; soluble CD4; Factor VIII; Factor IX; T-cell receptors; LDL receptor; ApoE; ApoC; alpha-1 antitrypsin; ornithine transcarbamylase (OTC); cystic fibrosis transmembrane receptor (CFTR); insulin; Fc receptors for antigen binding domains of antibodies, such as immunoglobulins; anti-HIV decoy tar elements; and antisense sequences which inhibit viral replication, such as antisense sequences which inhibit replication of hepatitis B or hepatitis non-A, non-B virus. The nucleic acid is chosen considering several factors, including the cell to be transfected. Where the target cell is a blood cell, for example, particularly useful nucleic acids to use are those which allow the blood cells to exert a therapeutic effect, such as a gene encoding a clotting factor for use in treatment of hemophilia. Another target cell is the lung airway cell, which can be used to administer nucleic acids, such as those coding for the cystic fibrosis transmembrane receptor, which could provide a gene therapeutic treatment for cystic fibrosis. Other target cells include muscle cells where useful nucleic acids, such as those encoding cytokines and growth factors, can be transduced and the protein the nucleic acid encodes can be expressed and secreted to exert its effects on other cells, tissues and organs, such as the liver. In addition, cancer cells corresponding or derived from lung, muscle, brain and other tissues can be target tissues. Furthermore, the nucleic acid can encode more than one gene product, limited only, if the nucleic acid is to be packaged in a capsid, by the size of nucleic acid that can be packaged.

The provided viral particles can be administered to cells, as described herein, with a Multiplicity of Infection (MOI) of 10. The MOI is the ratio of infectious virus particles to the number of cells being infected. Thus, an MOI of 0.1 results in the average inoculation of 1 virus particle for every 10 cells. The general theory behind MOI is to introduce one infectious virus particle to every host cell that is present in the culture. However, more than one virus may infect the same cell which leaves a percentage of cells uninfected. This occurrence can be reduced by using a higher MOI to ensure that every cell is infected. The provided viral particles can therefore be administered to cells, as described herein, with a MOI of 0.01 to 100, such as for example 1, 2, 3, 4, 5, 6, 7, 8, 9, 10, 11, 12, 13, 14, 15, 16, 17, 18, 19, 20, 30, 40, 50, 60, 70, 80, 90, 100.

The recombinant AAV vector is produced by recombinant methods utilizing multiple plasmids. In one example, the AAV1, AAV2, AAV5 or AAV6 recombinant viruses are produced using a three plasmid procedure previously described (Alisky et al., *Neuroreport*, 11: 2669-2673 (2000)). Briefly, semiconfluent HEK293T cells are transfected by calcium phosphate with three plasmids: an Ad helper plasmid containing the VA RNA, E2, and E4; an AAV helper plasmid containing the Rep and Cap genes for the serotype that is to be packaged; and a vector plasmid containing the inverted terminal repeats (ITRs) corresponding to the serotypes flanking a reporter gene of interest. Forty-eight hours posttransduction, the cells are harvested by scraping in TD buffer (140 mM NaCl, 5 mM KCl, 0.7 mM K2HPO4, 25 mM Tris-HCl pH 7.4) and the cell pellet concentrated by low-speed centrifugation. The cells that are efficiently transduced by all three plasmids, exhibit specific integration as well as the ability to produce the particular AAV recombinant virus of the present invention.

As defined herein, a functional portion or functional variant of the AAV6 vector, includes, for example, nucleotide sequences encoding any of the VA RNA, E2, E4, Rep, and Cap proteins, and fragments thereof.

The recombinant expression vector of the present invention comprises a native or normative promoter operably linked to the nucleotide sequence encoding a recombinant AAV6 viral genome and contains a heterologous nucleic acid sequence capable of being expressed by the host cell, or to the nucleotide sequence which is complementary to or which hybridizes to the nucleotide sequence encoding a recombinant AAV6 viral genome and containing a heterologous nucleic acid sequence capable of being expressed by the host cell, discussed above.

The selection of promoters, e.g., strong, weak, inducible, tissue-specific and developmental-specific, is within the ordinary skill of the artisan. Similarly, the combining of a nucleotide sequence with a promoter is also within the skill of the artisan. The promoter can be a non-viral promoter or a viral promoter, e.g., a cytomegalovirus (CMV) promoter, an SV40 promoter, an RSV promoter, and a promoter found in the long-terminal repeat of the murine stem cell virus.

The invention further provides a host cell comprising any of the recombinant expression vectors described herein. As used herein, the term "host cell" refers to any type of cell that can contain the inventive recombinant expression vector. The host cell can be an animal cell. Preferably, in an embodiment, the host cell is a mammalian cell. The host cell can be a cultured cell or a primary cell, i.e., isolated directly from an organism, e.g., a human. The host cell can be an adherent cell or a suspended cell, i.e., a cell that grows in suspension. Most preferably, the host cell is a human cell. The host cell can be of any cell type, can originate from any type of tissue, and can be of any developmental stage. Most preferably the host cells can include, for instance, muscle, lung, and brain cells, and the like.

The host referred to in the inventive methods can be any host. Preferably, the host is a mammal. As used herein, the term "mammal" refers to any mammal, including, but not limited to, mammals of the order Rodentia, such as mice and hamsters, and mammals of the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human.

In addition, the host cell can be a cancer cell. For example, in an embodiment, the host cell of the present can be a tumor cell, such as a tumor derived from the head or neck of a mammal, or a cell line derived from the head or neck of a mammal. With respect to the inventive methods, the cancer can be any cancer which expresses EGFR, including any of acute lymphocytic cancer, acute myeloid leukemia, alveolar rhabdomyosarcoma, bone cancer, brain cancer, breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva, chronic lymphocytic leukemia, chronic myeloid cancer, colon cancer, esophageal cancer, cervical cancer, gastrointestinal carcinoid tumor. Hodgkin lymphoma, hypopharynx cancer, kidney cancer, larynx cancer, liver cancer, lung cancer, malignant mesothelioma, melanoma, multiple myeloma, nasopharynx cancer, non-Hodgkin lymphoma, ovarian cancer, pancreatic cancer, peritoneum, omentum, and mesentery cancer, pharynx cancer, prostate cancer, rectal cancer, renal cancer (e.g., renal cell carcinoma (RCC)), small intestine cancer, soft tissue cancer, stomach cancer, testicular cancer, thyroid cancer, ureter cancer, and urinary bladder cancer. Preferably, the cancer is head or neck cancer.

Also provided by the invention is a population of cells comprising at least one host cell described herein. The population of cells can be a heterogeneous population comprising the host cell comprising any of the recombinant expression vectors described, in addition to at least one other cell, e.g., a host cell (e.g., a lung cell), which does not comprise any of the recombinant expression vectors, or a cell other than a lung cell, e.g., a skin cell, a neutrophil, an erythrocyte, a hepatocyte, an endothelial cell, an epithelial cell, a muscle cell, a brain cell, etc. Alternatively, the population of cells can be a substantially homogeneous population, in which the population comprises mainly of host cells (e.g., consisting essentially of) comprising the recombinant expression vector. The population also can be a clonal population of cells, in which all cells of the population are clones of a single host cell comprising a recombinant expression vector, such that all cells of the population comprise the recombinant expression vector. In one embodiment of the invention, the population of cells is a clonal population comprising host cells comprising a recombinant expression vector as described herein.

The recombinant vectors comprising the AAV6 viral genome and containing a heterologous nucleic acids sequence capable of being expressed by the host cell to be used for in vivo administration must be sterile. This is readily accomplished by, for example, filtration through sterile filtration membranes, prior to, or following reconstitution.

Therapeutic compositions generally are placed into a container having a sterile access port, for example, an intravenous solution bag or vial having a stopper pierceable by a hypodermic injection needle. The route of administration of the recombinant AAV vectors, in accordance with the present invention, is in accord with known methods, e.g., injection or infusion by intravenous, intraperitoneal, intramuscular, intraarterial, subcutaneous, intralesional routes, by aerosol or intranasal routes, or by sustained release systems as noted below. The recombinant AAV vectors, are administered continuously by infusion or by bolus injection.

An effective amount of recombinant AAV vector to be employed therapeutically will depend, for example, upon the therapeutic and treatment objectives, the route of administration, the age, condition, and body mass of the patient undergoing treatment or therapy, and auxiliary or adjuvant therapies being provided to the patient. Accordingly, it will be necessary and routine for the practitioner to titer the dosage and modify the route of administration, as required, to obtain the optimal therapeutic effect. A typical daily dosage might range from about $1 \times 10^4$ genomic particles/dose to about $1 \times 10^9$ genomic particles/dose or more, preferably from about $1 \times 10^6$ to about $1 \times 10^8$ genomic particles/dose, depending on the above-mentioned factors. Typically, the clinician will administer antibody until a dosage is reached that achieves the desired effect. The progress of this therapy is easily monitored by conventional assays.

The recombinant adeno-associated virus (AAV) vectors used in the context of the present invention can, themselves, be linked to a detectable label. Such a detectable label allows for the presence of, or the amount of the viral titer to be determined.

Alternative methods of vector delivery such as convection may enhance AAV6 distribution and, thus, more widespread tumor killing than the simple intratumoral injection. For example, an alternative method for efficient and widespread delivery of macromolecules and particles to tumors is convection-enhanced infusion, which is used to supplement simple diffusion and to improve vector distribution by bulk flow inside and outside the tumor. Stereotactic injection and subsequent infusion by maintaining a positive pressure gradient is able to improve the distribution of large molecules in animal models (Lieberman D. M., et al., *J. Neurosurg.* 82: 1021-1029 (1985)). In an embodiment, the present invention provides a method of treating a tumor which expresses EGFR in a mammal comprising administering to the mammal via convection-enhanced infusion, a therapeutically effective amount of a pharmaceutical composition comprising a recombinant AAV6 vector which encodes a gene that increases the host cell's susceptibility to a prodrug or cytotoxic agent, and administering to the mammal a therapeutically effective amount of a pharmaceutical composition comprising the specific prodrug or cytotoxic agent.

When applied, for example, to rat brain tumors, this convection-enhanced infusion technique was able to mediate delivery of virus particles to tumors with an approximate volume of 100 mm³, and also beyond the tumor borders into the surrounding brain tissue (Nilayer et al., *Proc. Natl. Acad. Sci. USA* 92: 9829-9833 (1995)).

Other methods of vector application include, for example, intravascular methods. Intravascular methods of vector application make use of a natural and ubiquitously distributed network of arteries, veins and capillaries, which is present in every normal tissue and is even denser in malignant tumors. Intravascular applications, such as intra-arterial injection of virus vectors, are capable of delivering a vector to the largest proportion of tumor cells and surrounding tissues without afflicting mechanical injury to normal brain tissue or having other toxic consequences (Spear et al., *J. Neurovirol.* 4: 133-147 (1998); Muldoon et al., "Delivery of therapeutic genes to brain and intracerebral tumors; in Chiocca E. A., and Breakefield X. O. (eds.), "Gene Therapy for Neurological Disorders and Brain Tumors," Boston: Humana Press, pp 128-139 (1997)). In an embodiment, the present invention provides a method of treating a tumor which expresses EGFR in a mammal, comprising administering to the mammal, via intravascular methods of vector application, a therapeutically effective amount of a pharmaceutical composition comprising a recombinant AAV6 vector which encodes a gene that increases the host cell's susceptibility to a prodrug or cytotoxic agent, and administering to the mammal a therapeutically effective amount of a pharmaceutical composition comprising the specific prodrug or cytotoxic agent.

Alternatively, in an embodiment, the present invention provides a method of treating a tumor which expresses EGFR in a mammal comprising administering to the mammal via intravascular methods of vector application, a therapeutically effective amount of a pharmaceutical composition comprising a recombinant AAV6 vector which encodes a gene that increases the host cell's susceptibility to a prodrug or cytotoxic agent, and administering to the mammal a therapeutically effective amount of a pharmaceutical composition comprising the specific prodrug or cytotoxic agent, in combination with one or more other pharmaceutically active agents or drugs, such as a chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive methods can provide any amount of any level of treatment or prevention of a disease in a mammal. Furthermore, the treatment or prevention provided by the inventive method can include treatment or prevention of one or more conditions or symptoms of the disease being treated or prevented. Also, for purposes herein, "prevention" can encompass delaying the onset of the disease, or a symptom or condition thereof.

The following examples further illustrate the invention but, of course, should not be construed as in any way limiting its scope.

EXAMPLES

Cell Cultures, rAAV production and transduction. The NCI60 cell line panel, and mouse IL-3-dependent myeloid cell line 32D, were maintained under standard culture conditions and cultured in RPMI media, 10% heat-inactivated fetal bovine serum (FBS), and 100 U/ml penicillin/streptomycin/amphotercin B (Invitrogen, Carlsbad Calif.). The 32D cells were further supplemented with 10 µg/ml IL-3 (Sigma, St. Louis Mo.). 32D cells were transfected with lipofectamine 2000 (Invitrogen) to deliver EGFR (ERBB1), ERBB2, ERBB3, or ERBB4 expression plasmids. Stably transfected 32D cells were selected for neomycin resistance, single cell populations were expanded and validated for specific isoform expression by western blot analysis. HN12, HN13 and HEp-2 cells were maintained under standard culture conditions and cultured in DMEM media, 10% heat-inactivated FBS, 100 U/ml penicillin/streptomycin/amphotercin B (Invitrogen).

Recombinant AAV1, AAV2, AAV5 and AAV6 were produced using a three plasmid expression system (See, Schmidt, M., et al., "Adeno-associated virus type 12 (AAV12): a novel AAV serotype with sialic acid- and heparan sulfate proteoglycan-independent transduction activity," *J. Virol.* 82: 1399-1406 (2008)). AAV was produced carrying either the Rous sarcoma virus long terminal repeat promoter driving expression of the nuclear localized beta-galactosidase reporter gene (RSV-NLS-LacZ), or nuclear-localized enhanced green fluorescent protein (NLS-eGFP), luciferase, or the herpes simplex virus 1 thymidine kinase transgene (HSVtk), driven by the cytomegalovirus early-immediate promoter, the driving protein promoter (CMV) and flanked by AAV2 inverted terminal repeats (ITR). In developing the seed data for COMPARE, the NCI60 cell line panel was transduced over a serial dilution with AAV6-RSV-NLS-LacZ. Transduction efficiency was measured by staining for beta-galactosidase expression in the transduced cells 60 hours posttransduction.

Comparative Gene Analysis. AAV6 transduction efficiency was measured in 48 cell lines within the NCI60 cell panel. Cells were transduced with AAV6-RSV-NLSLacZ vector over a serial dilution, and the averaged transduction efficiency was used as seed data for COMPARE as previously described (Di Pasquale, G., et al. Identification of PDGFR as a receptor for AAV-5 transduction. *Nat. Med.*, 9: 1306-1312 (2003)). The full AAV6 transduction profile data is available in the DTP database (http://dtp.nci.nih.gov/mtargets/mt_index.html) (See, Zaharevitz, D. W., Holbeck, S. L., Bowerman, C. & Svetlik, P. A., "COMPARE: a web accessible tool for investigating mechanisms of cell growth inhibition," *J. Mol. Graph. Model.* 20: 297-303 (2002)). COMPARE is a publicly available web-based data-mining tool offered by the Developmental Therapeutics Program (DTP), at the National Cancer Institute (NCI) (http://dtp.nci.nih.gov/compare/). The cDNA microarray data for the NCI60 cell line panel was used to identify genes with an expression pattern that highly correlated with the AAV6 transduction profile. A second software program, Microarray Analysis Program Package (MAPP) (Wilson, P. A., Microarray Analysis Perl Program (2007)), was used to further detail potential genes of interest by identifying alternative gene descriptors, subcellular location, and function specific for the COMPARE output format. The MAPP detailed gene data was then input into two pathway analysis software packages, Pathway Architect (Stratagene, La Jolla Calif.) and ExPlain (Biobase International, Wolfenbüttel, Germany), to visualize connectivity of genes that positively correlate with AAV6 transduction. The use of multiple pathway mapping software packages compensated for the variability in mapping algorithms and coverage of signal transduction pathway of each program.

AAV transduction and pharmacological inhibition. The 32D and 32D-EGFR cells were transduced with 1.0E4 genomic particle (gp)/cell with each of the AAV serotypes tested. Cells were analyzed for GFP expression by FACS analysis at 96 hours posttransduction. The HEK293T, HN12 and HEp-2 cells, shown to be permissive to AAV2 and/or AAV6, were used to evaluate the specific role of EGFR in AAV-mediated transduction. Cells were incubated at 37° C. in the presence or absence of AG1478 (10 µm) or gefitnib (10 µm) for 30 minutes prior to addition of AAV. AAV2 and AAV6 containing the CMV-NLS-eGFP construct were added at a concentration of $1.0 \times 10^4$ gp/ml for 90 minutes. Cells were gently washed to remove excess, non-bound virus, and GFP expression was analyzed by FACS 48 hours post transduction for HEK293T cells, or 96 hours post transduction for HN12 and HEp-2 cell lines.

siRNA knockdown of EGFR expression. siRNA against EGFR was used to knockdown EGFR expression in HEK293T and HN13 cells. The EGFR siRNA (Qiagen, Valencia Calif.; #S100074053) and the Allstars negative siRNA control (Qiagen, #1027280), were added to cells as per manufacturer's protocol. Cultures were incubated for 48 hours prior to transduction with AAV6 containing the CMV-NLS-eGFP construct at a concentration of 1.0E4 gp/cell. Cells were analyzed for transgene expression 48 hours post transduction by FACS analysis.

AAV Internalization. 32D-EGFR cells were incubated with either AAV2 or AAV6-CMV-NLS-eGFP in the presence or absence of 10 m AG1478 for 90 minutes at 37° C. Cells were gently washed to remove excess, non-bound virus and incubated with 0.5% trypsin to removed remaining extracellular virus. Intracellular DNA was isolated and copies of vector genome/cell population were quantified by QPCR as described previously (Di Pasquale, G., et al.).

Specific Co-precipitation of AAV6 and EGFR. The rhEGFR-Fc or rhFGFRFc chimeric soluble proteins (R&D Systems, Minneapolis, Minn.; 5 g protein) were coupled with a 10% solution of protein-A sepharose beads (Sigma) in PBS, containing 1% BSA and 0.1% pluronic acid, at 4° C. for 4 hours with gentle agitation. AAV was added ($1.0 \times 10^9$ gp) to the soluble receptor-sepharose bead complex solution and incubated at 4° C. with gentle agitation for 90 minutes. Beads were centrifuged and extensively washed to remove excess, non-bound protein and AAV. Viral DNA was isolated and copies of vector genome were quantified by QPCR (Di Pasquale, G., et al.). As a measure of non-specific AAV binding, sepharose beads and AAV were incubated for similar durations and conditions, in the absence of rhEGFR-Fc, or rhFGFR-Fc.

Animal Studies. All animal studies were carried out according to NIH-approved protocols, in compliance with the Guide for the Care and Use of Laboratory Animals. Female athymic (nu/nu) nude mice (Harlan Sprague-Dawley), 5 to 6 weeks old and weighing 18 to 20 g, were used in the study, housed in appropriate sterile filter-capped cages, and fed and given water ad libitum. Head and neck tumor cell lines, HN12 and HEp-2 ($2.0 \times 10^6$ cells/injection), were injected subcutaneously into both the right and left flank of nude mice to establish xenograft tumors. After tumors were established (7-10 days), AAV6-CMV-luciferase or AAV6-CMV-HSVtk ($4.0 \times 10^9$ gp/40 ul) was injected into the flank tumors. Luciferase transgene expression was measured 10 days post AAV6 treatment by intraparatoneal injection of luciferin (4 mg/100 ml in PBS). Bioluminescence was imaged using the IVIS Xenogen imaging system (Xenogen, Alemeda Calif.) to measure luciferase expression in vivo. Regions of interest were quantified as mean average radiance (photons/s/cm$^2$/sr) using Living Image software tools (Xenogen). To quantify copies of vector genome/mg tumor tissue, DNA was isolated from 25-35 mg samples of tumor tissue and copies vector genome were quantified by QPCR17. Copies vector genome/mg tissue of HN12 or HEp-2 tumors that only received vehicle control was used a background control and subtracted from vector genome/mg tumor tissue calculated for tumors that received intratumoral AAV6-CMV-luciferase injections.

For the gene-directed enzyme prodrug therapy (GDEPT) study, tumors were injected with AAV6-CMV-HSVtk (4.0E9 genomic particles/40 μl) or equal volume of vehicle (0.9% saline). Ganciclovir (Sigma) (50 mg/kg/day) was delivered via intraparatoneal injections daily. Tumor volume was measured as previously described (See, Amornphimoltham, P., et al., "Mammalian target of rapamycin, a molecular target in squamous cell carcinomas of the head and neck," Cancer Res. 65: 9953-9961 (2005)). Length (L) and width (W) of tumor were determined and volume was calculated using the following equation: $(L*W_2)/2$. Percent tumor growth was calculated as tumor volume at each time point per volume prior to start of ganciclovir treatment. Tumors were measured until day 20 at which time the size of the untreated tumors required ethical termination of the study.

There was no significant difference in tumor volume noted between tumors that received AAV6 and those that did not prior to starting ganciclovir treatment (data not shown). Additionally, there was no significant difference in percent tumor growth of tumors that received AAV6-CVM-HSVtk and no ganciclovir treatment and those tumors that were not transduced by AAV6 but did receive ganciclovir treatment (data not shown).

Statistical Analysis. We analyzed the statistical significance of the linear relationship between AAV6 transduction and gene expression patterns using Pearson correlation coefficient (PCC) calculated through the COMPARE program, and verified statistical significance of EGFR (GC16216) using correlation analysis with Prism software (Graphpad, La Jolla Calif.). All data is presented as means+/−s.e.m. Statistical significance was calculated using unpaired Student's t-test.

Example 1

This example discloses how CGA was used to identify correlations between viral transduction profiles and gene expression profiles across the NCI60 cell panel.

Figure 1:
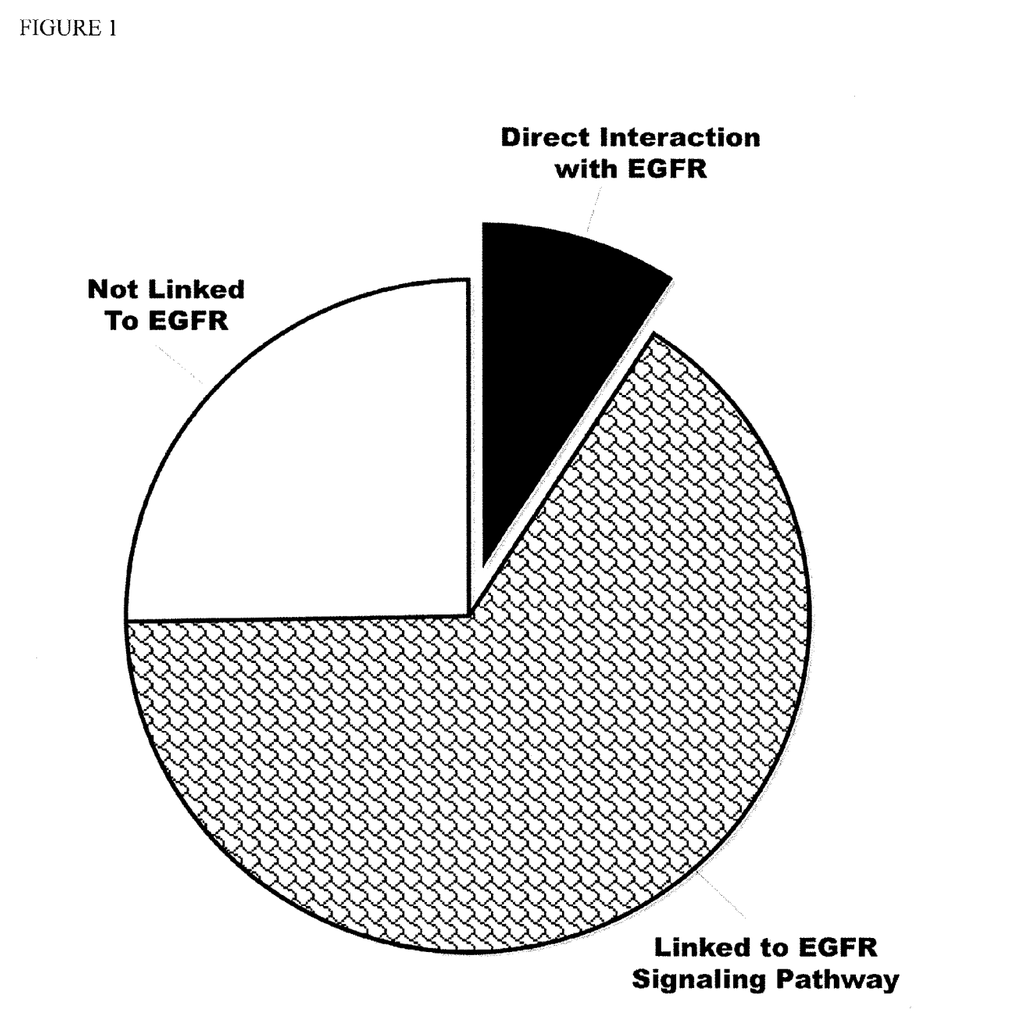
FIG. 1 is a pie chart illustrating that of the top 1000 genes returned by the program COMPARE, 760 genes were associated with identifiable gene names, of which 226 genes had established pathway interactions. Of these genes with known pathway interactions, 169 (75%) were found to be involved in EGFR signaling, with 21 (9%) having a direct interaction with, or regulation of, the EGF receptor (ERBB1).

Building upon the established CGA method, additional bioinformatics-based software and pathway visualization packages were added, to further prioritize potential AAV cell surface receptors. The expression data and Pearson correlation coefficient (PCC) values were obtained from the Developmental Therapeutics Program online database and web-accessible COMPARE program. Of the top 1000 genes returned by COMPARE, 760 genes were associated with identifiable gene names, of which 226 genes had established pathway interactions. Of these genes with known pathway interactions, 169 (75%) were found to be involved in EGFR signaling with 21 (9%) having a direct interaction with or regulation of the EGF receptor (ERBB1) (FIG. 1).

A positive correlation between EGFR expression (DTP microarray pattern identification number GC16212) and cells permissive to AAV6 (PCC value of 0.421, P=0.003) was identified. Our discovery of extensive clustering of positive PCC genes connected to the EGFR signaling pathway provided the basis for further studies on the involvement of EGFR or its downstream signaling pathways in AAV6 transduction.

Example 2

To confirm whether the in silico findings would translate to activity in vivo, the influence of EGFR expression on AAV6 transduction was studied.

Figure 2:
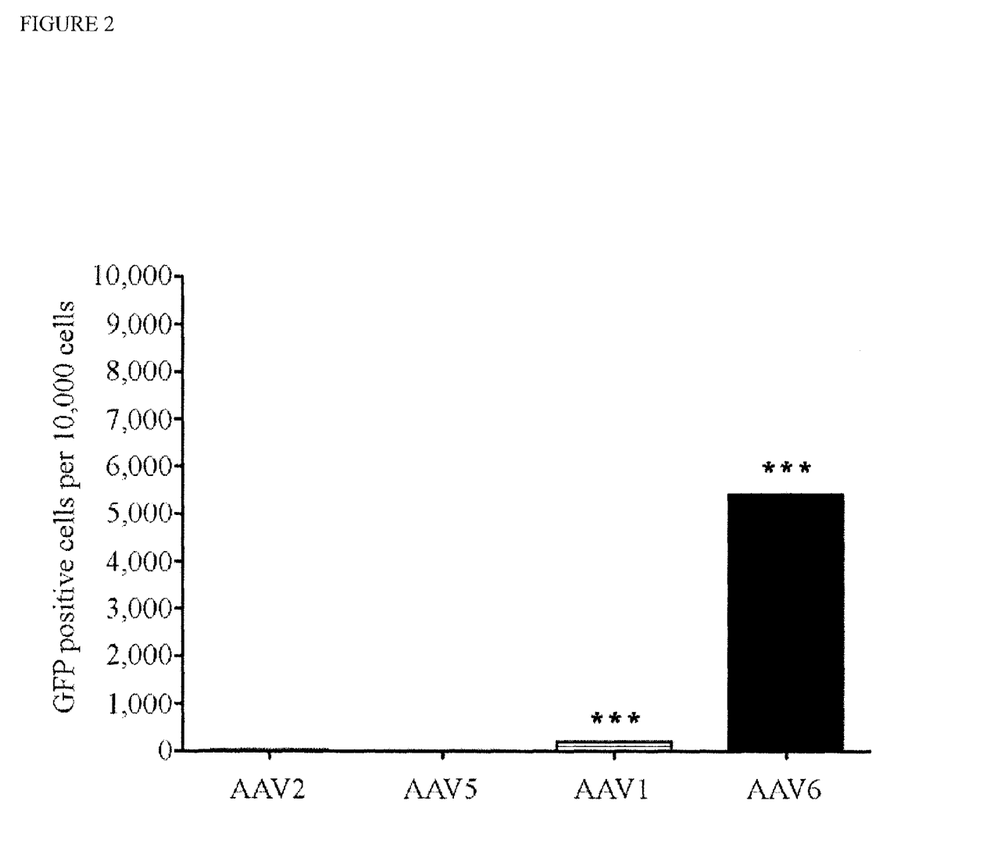
FIG. 2 is a graph showing the quantification of FACS analysis of 32D-EGFR cells 96 hours after transduction with AAV2, AAV5, AAV1 or AAV6-CMV-EGFP. ***P<0.0001, n=3.

Initially, 32D cells, an IL-3-dependent hematopoietic progenitor cell line, which lack EGFR expression to stably express EGFR (32D-EGFR), were transduced with multiple AAV serotypes. Wild-type 32D cells were not permissive for any of the serotypes tested. In the presence of EGFR, AAV6 was able to efficiently transduce about 54.1±0.3% of the 32D-EGFR cells (FIG. 2). Like AAV6, AAV1 was able to transduce the 32D-EGFR cells, but to a lesser extent suggesting additional molecules may be necessary for optimal transduction activity with this vector. The lack of transduction by AAV2 or AAV5 in the presence or absence of EGFR suggests EGFR specificity for AAV6-like viruses.

Example 3

Figure 3:
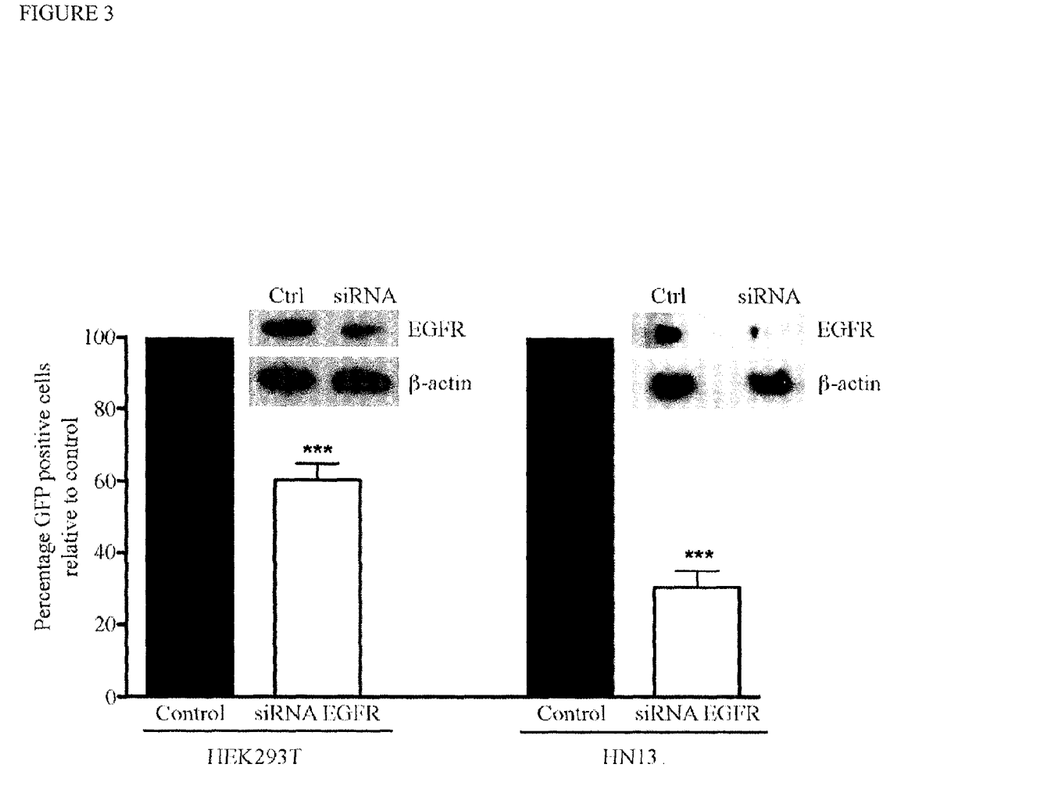
FIG. 3 shows two graphs that depict HEK293T and HN13 cells that were transfected with EGFR and siRNA against EGFR. Expression levels were quantified by western blotting, and the results are expressed as the percentage which are positive for GFP relative to controls. Cells were transduced by AAV2 or AAV6-CMV-eGFP (***P<0.0001, n=3).

In this example, EGFR-specific siRNA was used to knock down EGFR expression, and evaluate the impact on AAV transduction in two cell lines, HEK293T cells and HN13 cells, human embryonic kidney and head-and-neck tumor cell lines, respectively. Expression levels were quantified by western blotting, and the results are expressed as the percentage which are positive for GFP relative to controls. Cells were transduced by AAV2 or AAV6-CMV-eGFP (***$P<0.0001$, n=3). In HEK293T and HN13 cells, EGFR expression was knocked down by 37% and 58%, respectively, with EGFR-specific siRNA and, in accordance, corresponded with a 40% and 70% decrease in transduction, respectively (FIG. 3).

Example 4

To better understand the role of EGFR in AAV6 transduction, AAV6 vector transduction was measured in the presence or absence of the EGFR inhibitors AG1478 or gefitinib.

Figure 4:
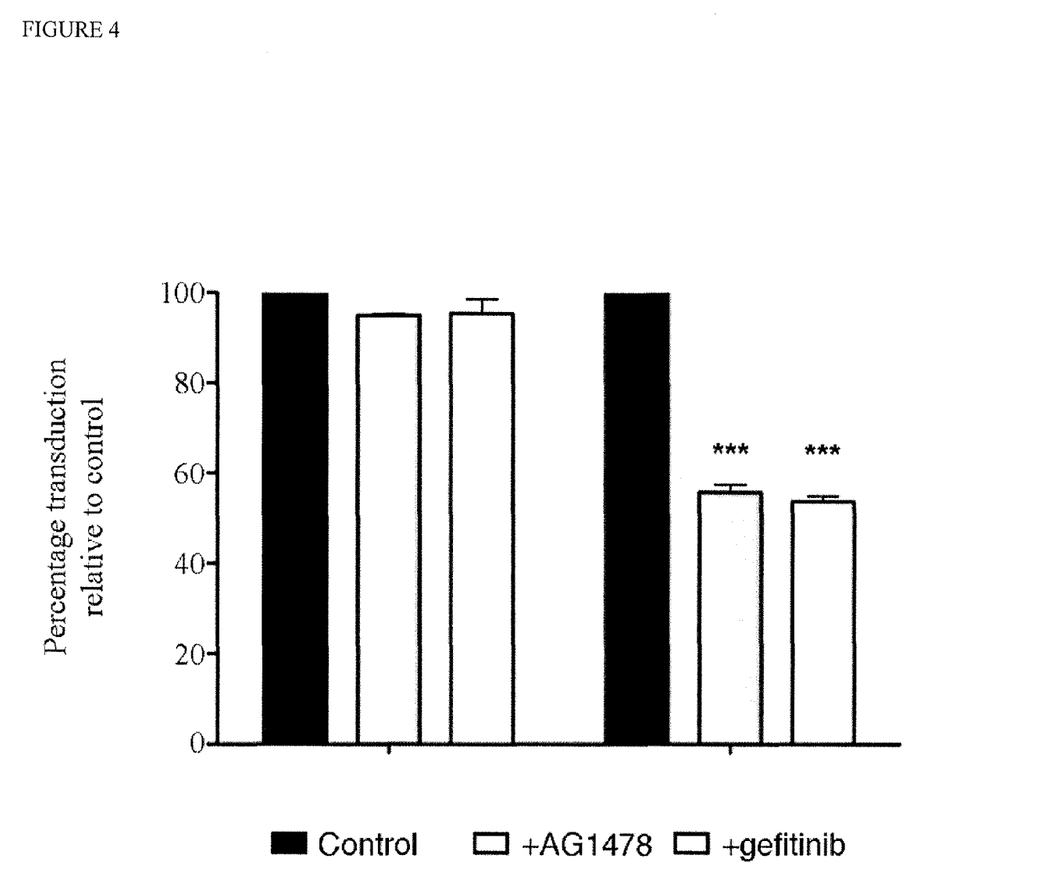
FIG. 4 is a FACS analysis of HEK293T cells preincubated with one of the EGFR-specific inhibitors, AG1478 (Tyrphostin) or gefitinib (Iressa®, 4-(3-Chloro-4-fluorophenylamine)-7-methoxy-6(3-(4-morpholinyl)quinazoline), and subsequently incubated with AAV6-CMV-eGFP, to evaluate the impact of EGFR function on AAV6 mediated transduction. AAV2 transduction was not significantly influenced by EGFR inhibition. ***P<0.0001, n=3.

HEK293T cells were preincubated with one of the EGFR-specific inhibitors, AG1478 (Tyrphostin) or gefitinib (Iressa®, 4-(3-Chloro-4-fluorophenylamine)-7-methoxy-6-(3-(4-morpholinyl)quinazoline), and subsequently incubated with AAV6-CMV-eGFP, to evaluate the impact of EGFR function on AAV6 mediated transduction. AAV2 transduction was not significantly influenced by EGFR inhibition. ***$P<0.0001$, n=3. AAV6 transduction of HEK293T cells was inhibited by 50% in the presence of either inhibitor. Under the same conditions, AAV2 transduction was unchanged (FIG. 4).

Example 5

This example shows that EGFR is necessary for AAV6 internalization.

Figure 5A:
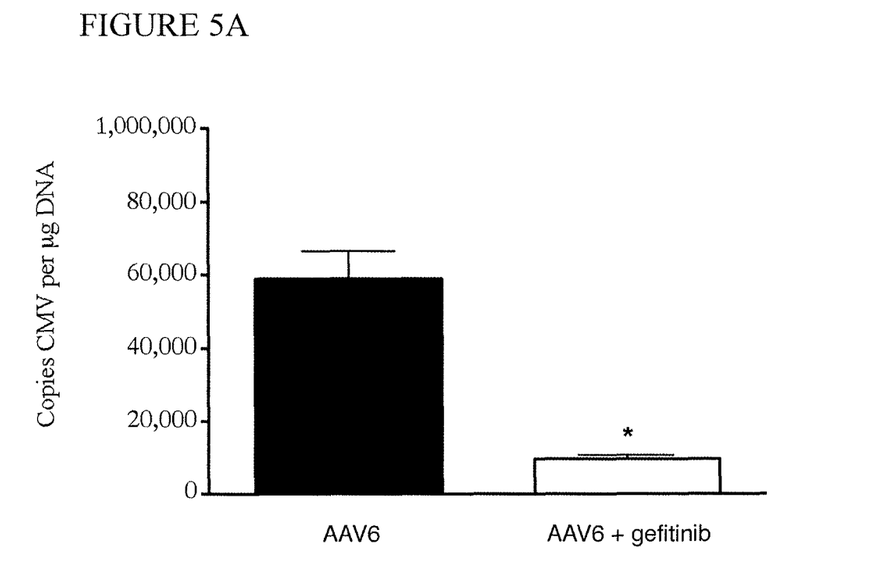
FIG. 5A is a graph showing internalization of AAV6 in 32D-EGFR cells. Internalization was measured in the presence or absence of gefitinib to evaluate the impact of function EGFR on AAV6 internalization. *P<0.01, n=3.

Internalization was measured in the presence or absence of gefitinib to evaluate the impact of function EGFR on AAV6 internalization. *$P<0.01$, n=3. Further analysis suggested that EGFR is involved in vector entry, as AAV internalization was decreased by over 500% in the presence of gefitinib (FIG. 5A). These results suggest that functional signaling through EGFR is required for AAV6 transduction and vector internalization.

Example 6

Although the above data suggest a direct interaction between EGFR and AAV6, EGFR could be functioning as a part of a complex, or AAV6 could be using the same trafficking pathway as EGFR.

Figure 5B:
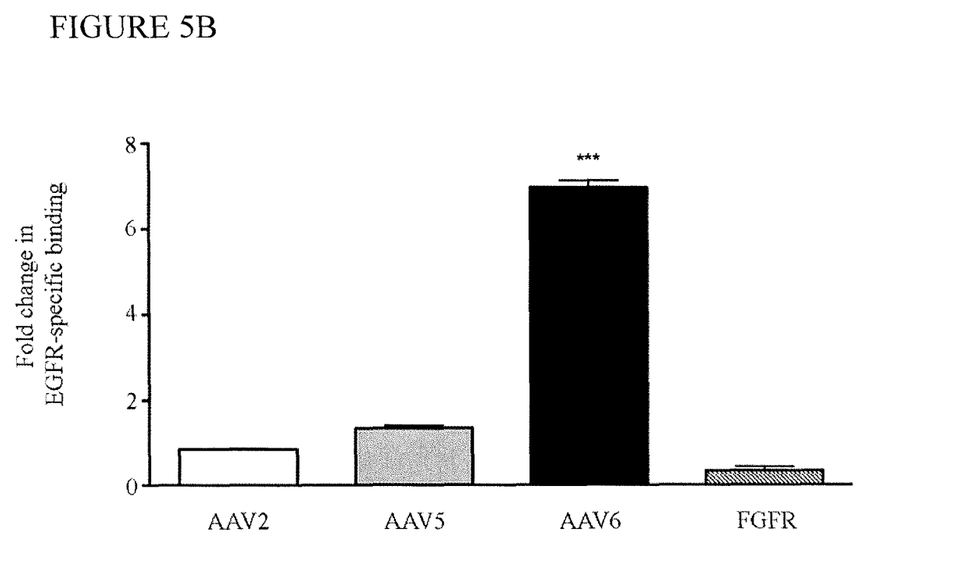
FIG. 5B is a graph depicting immunoprecipitation of AAV after incubating AAV2, AAV5, or AAV6 with protein A-sepharose beads alone, or with beads precoated with rhEGFR-Fc, or rhFGFR-Fc. ***P<0.0001, n=3.

To measure direct EGFR-AAV6 interaction, soluble recombinant human EGFR-Fc fusion protein (rhEGFR-Fc) or soluble FGFR (rhFGFR-Fc) was prebound to protein A-sepharose beads, and then they were incubated with AAV2, AAV5 or AAV6. Of the three serotypes used, AAV6 binding increased approximately sevenfold in the presence of rhEGFR-Fc (FIG. 5B). No significant increase in EGFR specific binding with AAV2 or AAV5 was observed. Furthermore, AAV6 did not bind to rhFGFR-Fc-coated beads (FIG. 5B), suggesting a specific AAV6-EGFR interaction.

Example 7

Figure 6:
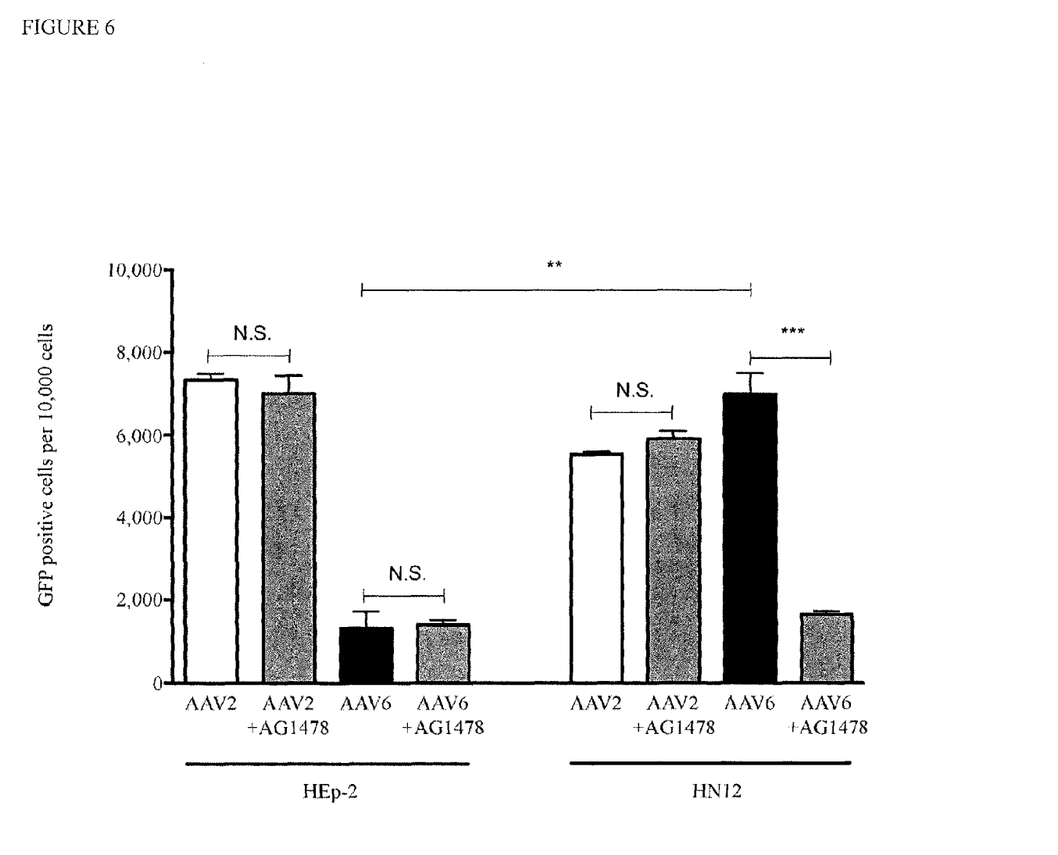
FIG. 6 shows that AAV6 transduces tumor cells with functional EGFR expression. In vitro transduction of HEp-2 and HN12 cells with AAV2 and AAV6 in the presence or absence of the EGFR inhibitor, AG1478, was studied. A statistically significant increase in AAV6-mediated transduction was found in HN12 cells compared to HEp-2 cells (p<0.001, n=3). Transduction of HN12 cells in the presence of AG1478 was reduced by 77% (*p<0.0005, n=3). An increase in AAV2-mediated transduction in HEp-2 cells compared to HN12 cells was noted (**p<0.001, n=3). There was no significant (NS) difference in AAV2-mediated transduction of HEp-2 or HN12 cells in the presence or absence of AG1478.

Increased expression of EGFR correlates with aggressive head and neck squamous cell carcinoma (HNSCC) tumor growth and resistance to treatment (Thariat, J., et al., Int. J. Clin. Oncol., 12: 99-110 (2007)). The utility of AAV6 to transduce and ablate specific HNSCCs presenting with elevated EGFR expression was assessed by gene-directed enzyme prodrug therapy. Two HNSCC cell lines, HN12 and HEp-2 were selected to represent polarities of EGFR expression. HN12 cells express a higher level of membrane-localized EGFR compared with HEp-2 cells, which express a lower, more diffuse pattern of EGFR expression (Magné, N., et al., Br. J. Cancer, 86: 1518-1523 (2002). In preliminary in vitro studies, HN12 cells showed an EGFR-dependent AAV6 transduction, whereas HEp-2 cells were markedly less permissive to AAV6. Transduction of HEp-2 cells was not altered in the presence of AG1478 (FIG. 6).

Example 8

In this example, in order to evaluate the AAV6-EGFR interaction in vivo, xenograft tumor models of these two cell lines were developed in female athymic (nu/nu) nude mice.

Figure 7:
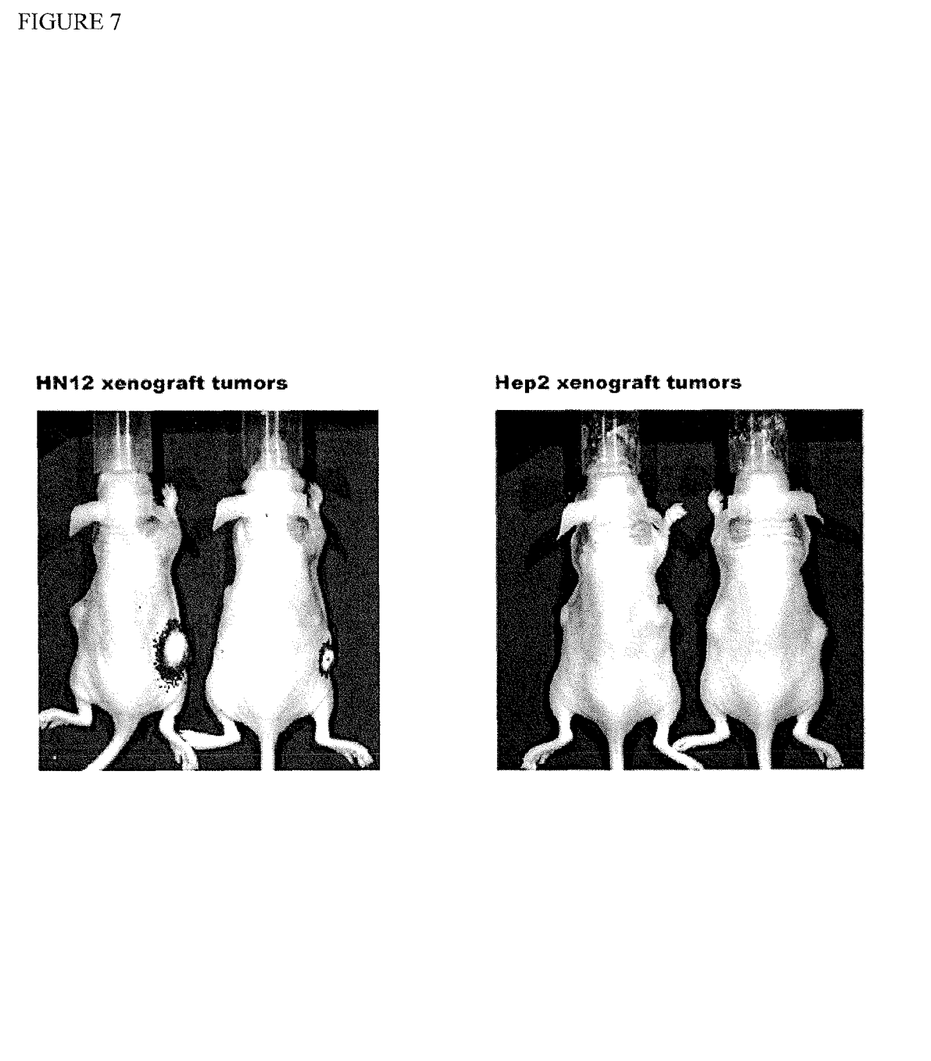
FIG. 7 depicts photographs showing evidence of AAV6 mediated transduction of EGFR expressing tumors and delivery of the cytotoxic transgene, HSVtk, followed by ganciclovir treatment, results in a significant reduction in tumor growth. Head and neck tumor cell lines, HN12 and HEp-2, were injected subcutaneously into the right and left flank of female nude mice. After tumors were established, AAV6-CMV-luciferase was introduced by direct intratumoral injection to the right flank tumors, with the vehicle control injected into the left flank tumors. Ten days after AAV administration, in vivo luciferase activity was measured by bioluminescence after intraperitoneal injection of luciferin (representative images, n=5).
Figure 8:
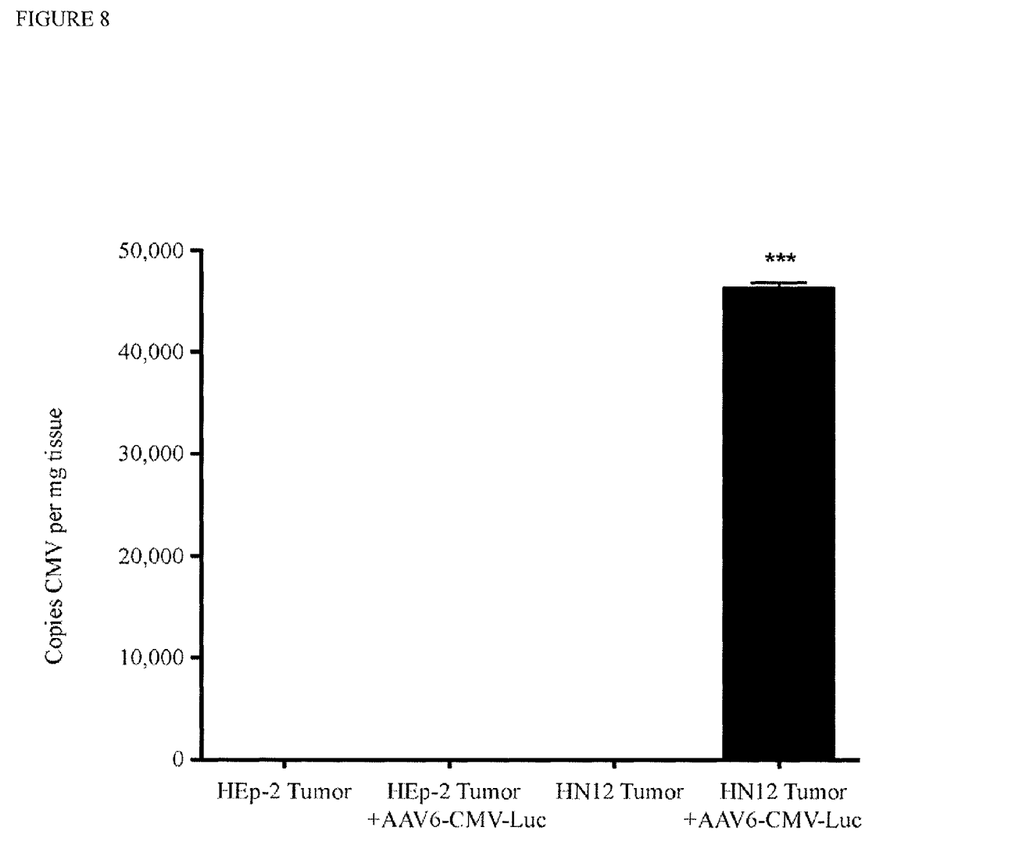
FIG. 8 shows that AAV6 is able to deliver transgene to HNSCC xenograft tumors with high expression of EGFR. To further verify AAV-mediated transduction of the HNSCC tumors in the xenograft model, HN12 and HEp-2 tumor tissue was isolated and presence of transgene was quantified. Total DNA was isolated from tumors that received AAV6-CMVLuciferase (AAV6-CMV-Luc), or vehicle control, and the number of copies of vector genome/mg tissue were quantified by QPCR. HN12 tumors injected with AAV6-CMV-luciferase contained $4.6 \times 10^4 \pm 0.1 \times 10^4$ copied vector genome/mg tissue. In contrast, AAV6-CMV-luciferase vector in HEp-2 cells was at background. ***$p<0.0001$, n=3.

The mouse tumors were intratumorally injected with AAV6 containing a luciferase transgene under control of a cytomegalovirus immediate early promoter (AAV6-CMV-Luciferase). Upon receiving an intraperitoneal injection of solution containing luciferin (the chemical substrate for luciferase protein), the HN12 tumors that received AAV6-CMV-luciferase showed a significantly elevated (15-fold) average radiance of $1.01 \times 10^4 \pm 0.31 \times 10^4$ photons s-1 cm-2 sr-1, after subtraction of average background radiance, compared with the Hep-2 tumors ($0.69 \times 10^3 \pm 0.48 \times 10^3$ photons s-1 cm-2 sr-1) (FIG. 7). This difference in transduction activity was also confirmed by quantification of vector genomes isolated from the tumors (FIG. 8). The ability of AAV6 to efficiently transduce EGFR-expressing tumors in vivo presented an opportunity to target and deliver cytotoxic transgenes to HN12 tumors highly expressing membrane-localized EGFR.

Example 9

This example tests whether the specificity and tropism of AAV6 for EGFR expressing HN12 cells was sufficient to ablate tumor growth without damaging the surrounding EGFR-expressing muscle.

Figure 9:
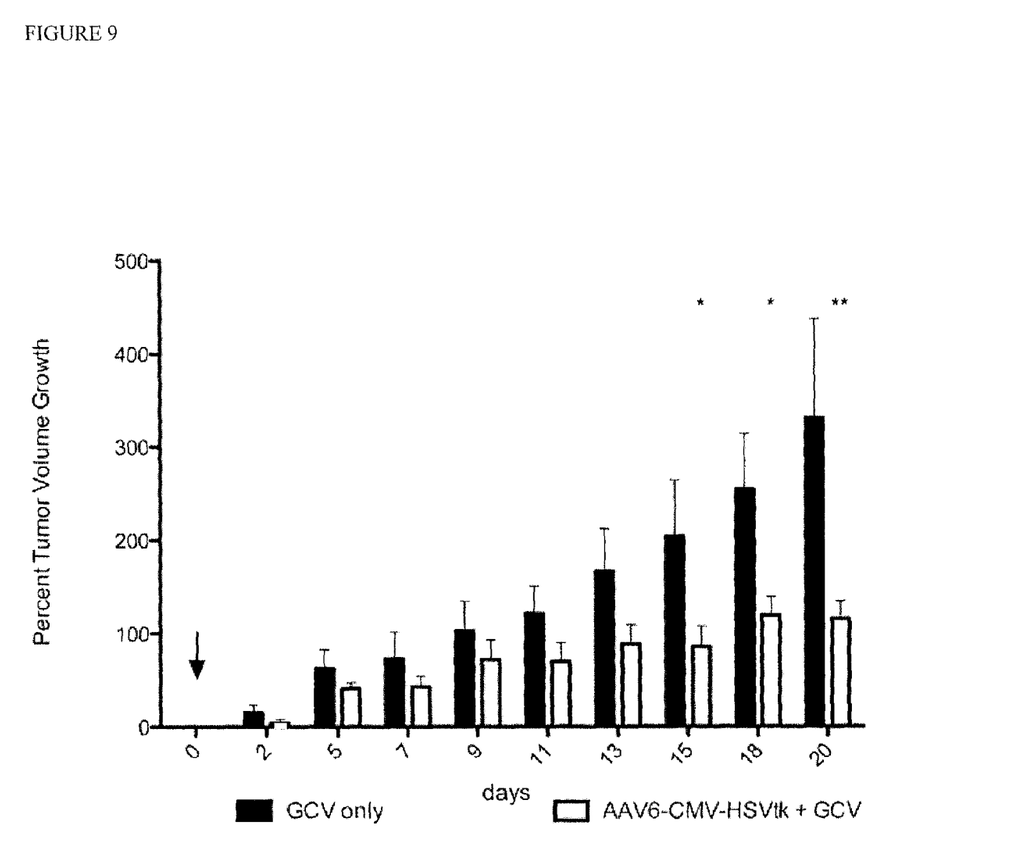
FIG. 9 is a graph depicting the percentage growth of HN12 tumors injected with AAV6-CMV-HSVtk, followed by ganciclovir (GCV) treatment, and HN12 tumors treated with GCV alone. The HN12 xenograft tumors received intratumoral injections of AAV6-CMV-HSVtk. One week after AAV6 transduction, mice were started on daily GCV injections. Arrow indicates day GCV treatment was started. *$P<0.05$, **$P<0.001$, n=9.

HN12 xenograft tumors were injected with AAV6 vectors encoding herpes simplex virus thymidine kinase (HSVtk) followed 7 days later by treatment with ganciclovir. At the culmination of the study (day 20), we observed a 65% reduction in tumor growth between tumors transduced with AAV6-CMV-HSVtk vector and treated with ganciclovir and tumors that received only ganciclovir treatment (FIG. 9).

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of treating a tumor in a mammal, wherein the tumor comprises epidermal growth factor receptor (EGFR)-expressing cells, the method comprising:
   directly administering to the tumor a therapeutically effective amount of a pharmaceutical composition comprising a recombinant adeno-associated virus (AAV) vector comprising the AAV subtype 6 (AAV6) viral genome, or a functional portion thereof, and containing a heterologous nucleic acid sequence comprising a gene encoding a polypeptide or protein that converts a prodrug into a cytotoxin that kills the EGFR-expressing cells; and
   administering to the mammal a therapeutically effective amount of a pharmaceutical composition comprising the prodrug,
   wherein administering (i) the vector and (ii) the prodrug treats the tumor.

2. The method of claim 1, wherein the tumor is a head or neck tumor.

3. The method of claim 1, wherein the heterologous nucleic acid comprises a gene encoding a polypeptide or protein selected from the group consisting of: E. coli nitroreductase, cytosine deaminase, Varicella Zoster-tk, Cytochrome P450 B1 (CYP2B1), carboxypeptidase G2 (CPG2), E. coli purine nucleoside phosphorylase (ePNP), and Herpes Simplex Virus thymidine kinase (HSV-tk).

4. The method of claim 1, wherein the gene encodes HSV-tk.

5. The method of claim 4, wherein the prodrug is ganciclovir.

6. The method of claim 5, wherein the tumor is a head or neck tumor.

7. The method of claim 5, wherein there is a delay of a period of time between administering the therapeutically effective amount of the pharmaceutical composition comprising the recombinant AAV6 vector and administering the therapeutically effective amount of the pharmaceutical composition comprising the ganciclovir.

8. The method of claim 5, further comprising administering to the mammal a therapeutically effective amount of a pharmaceutical composition comprising a second prodrug.

9. The method of claim 5, wherein the method comprises specifically transducing the EGFR-expressing cell with the recombinant AAV6 vector.

10. The method of claim 9, wherein the EGFR-expressing cells are transduced with the vector and non-EGFR-expressing cells are not transduced with the vector.

11. The method of claim 10, wherein the transduced EGFR-expressing cells contain $4.6 \times 10^4 \pm 0.1 \times 10^4$ copies of the vector genome per mg of tissue.

12. The method of claim 1, wherein the prodrug is a nucleotide analog.

13. The method of claim 1, wherein the prodrug is ganciclovir.

14. The method of claim 1, wherein there is a delay of a period of time between administering the therapeutically effective amount of the pharmaceutical composition comprising the recombinant AAV6 vector and administering the therapeutically effective amount of the pharmaceutical composition comprising the prodrug.

15. The method of claim 1, further comprising administering to the mammal a therapeutically effective amount of a pharmaceutical composition comprising a second prodrug.

16. The method of claim 1, wherein the method comprises specifically transducing the EGFR-expressing cell with the recombinant AAV6 vector.

17. The method of claim 16, wherein the EGFR-expressing cells are transduced with the vector and non-EGFR-expressing cells are not transduced with the vector.

18. The method of claim 17, wherein the transduced EGFR-expressing cells contain $4.6 \times 10^4 \pm 0.1 \times 10^4$ copies of the vector genome per mg of tissue.

* * * * *